(12) United States Patent
Cheng et al.

(10) Patent No.: US 10,571,430 B2
(45) Date of Patent: Feb. 25, 2020

(54) GAS CONCENTRATION SENSORS AND SYSTEMS

(71) Applicant: Veeco Instruments Inc., Plainview, NY (US)

(72) Inventors: Chi-Jung Cheng, Somerset, NJ (US); Leo Chin, Poughquag, NY (US); Christopher J. Morath, Basking Ridge, NJ (US); Arindam Sinharoy, Furlong, PA (US); Raymond C. Logue, Henderson, NV (US)

(73) Assignee: Veeco Instruments Inc., Plainview, NY (US)

( * ) Notice: Subject to any disclaimer, the term of this patent is extended or adjusted under 35 U.S.C. 154(b) by 114 days.

(21) Appl. No.: 15/455,678

(22) Filed: Mar. 10, 2017

(65) Prior Publication Data

US 2017/0261471 A1   Sep. 14, 2017

Related U.S. Application Data

(60) Provisional application No. 62/307,798, filed on Mar. 14, 2016.

(51) Int. Cl.
*G01N 29/024* (2006.01)
*G01N 29/44* (2006.01)

(52) U.S. Cl.
CPC ....... *G01N 29/024* (2013.01); *G01N 29/4463* (2013.01); *G01N 2291/011* (2013.01); *G01N 2291/0212* (2013.01)

(58) Field of Classification Search
CPC ............. G01N 29/024; G01N 29/4463; G01N 2291/011; G01N 2291/0212; G01N 2291/021; G01N 29/02; G01N 29/2437; G01N 29/2425; G01N 29/24
USPC .................................. 73/24.01–24.04, 24.06
See application file for complete search history.

(56) References Cited

U.S. PATENT DOCUMENTS

| | | | | |
|---|---|---|---|---|
| 5,673,562 | A | * | 10/1997 | Friedt ...................... F17C 7/04 62/48.1 |
| 6,279,379 | B1 | | 8/2001 | Logue et al. |
| 6,492,625 | B1 | | 12/2002 | Boguslavskiy et al. |
| 6,506,252 | B2 | | 1/2003 | Boguslavskiy et al. |
| 6,895,825 | B1 | * | 5/2005 | Barkhoudarian ....... G01F 1/662 73/861.28 |
| 6,902,623 | B2 | | 6/2005 | Gurary et al. |
| 8,021,487 | B2 | | 9/2011 | Boguslavskiy et al. |
| 8,092,599 | B2 | | 1/2012 | Sferlazzo et al. |
| 8,133,322 | B2 | | 3/2012 | Nakamura et al. |

(Continued)

OTHER PUBLICATIONS

316L Stainless Steel Product Data Bulletin, AK Steel (Year: 2016).*

*Primary Examiner* — Suman K Nath
(74) *Attorney, Agent, or Firm* — Patterson Thuente Pedersen, P.A.

(57) ABSTRACT

A chemical vapor deposition or atomic layer deposition system includes a gas concentration sensor for determining the quantity of precursor gases admitted thereto. The gas concentration sensor can include a transmitter and a receiver for transmitting an acoustic signal across a chamber. In embodiments, the transmitter and receiver are designed to increase transmitted signal while reducing transmitted noise, facilitating use of the gas concentration sensor at low pressure and high temperature.

10 Claims, 12 Drawing Sheets

(56) References Cited

U.S. PATENT DOCUMENTS

| | | | |
|---|---|---|---|
| 2003/0173870 A1* | 9/2003 | Simon Hsu | B06B 1/0611 |
| | | | 310/334 |
| 2004/0060518 A1 | 4/2004 | Nakamura et al. | |
| 2004/0175939 A1 | 9/2004 | Nakamura et al. | |
| 2007/0186853 A1 | 8/2007 | Gurary et al. | |
| 2012/0040097 A1 | 2/2012 | Volf et al. | |
| 2016/0338199 A1* | 11/2016 | Hua | H01R 12/52 |

\* cited by examiner

GAS CONCENTRATION SENSORS AND SYSTEMS

CROSS-REFERENCE TO RELATED APPLICATION

This application claims the benefit of priority to U.S. Provisional Patent Application Ser. No. 62/307,798 (filed Mar. 14, 2016), the contents of which are incorporated by reference herein in their entirety.

TECHNICAL FIELD

The invention relates generally to acoustical system for sensing concentration of precursor gases used in semiconductor manufacturing processes. More particularly, the invention relates to new improvements of materials and bonding methods which allow sensor to be used in wider temperature and pressure ranges.

BACKGROUND

In the field of semiconductor and LED manufacturing, vapor deposition processes such as Chemical vapor deposition (CVD), Metal-Organic Chemical Vapor Deposition and Atomic layer deposition (ALD) have played a critical role in depositing materials on substrates. All these processes require accurate delivery of precursor gas into reactor chamber in order to create a desired uniformity and quality of the layer on the substrate. Accurate delivery of such gas/vapor mixture requires precise measurement of the concentration of the precursor gas.

At present there is a wide variety of concentration sensors are available in market which use different sensing techniques such as acoustical technology, optical technology and mass spectroscopy. Among these technologies; the acoustical sensor such as PIEZOCON® gas concentration sensor (hereinafter "Piezocon Sensor") sold by VEECO has demonstrated high accuracy and repeatable real time concentration measurement. It has been widely used and integrated in CVD and MOCVD tools for monitoring the precursor concentration and controlling the mass flow.

In the conventional Piezocon systems, a piezoelectric component is stacked on each side of the transducer, and mechanically coupled to a transformer. The interface between the piezoelectric components and the transformer is an epoxy that provides a mechanical bonding and also permits for the transmission of acoustic signal. However, despite the mechanical structure of the sensor being robust, it has been discovered that the piezoelectric components can separate from the transformer when the sensor is operated at a relatively high temperature (>100° C.). This is due to the coefficient of thermal expansion (CTE) mismatch between piezoelectric components and transformer, which causes mechanical deformation, stress and strain between components that result in mechanical bonding failures.

In addition to the mechanical challenge of the sensor at high temperature, it has been also discovered that the accuracy of measurement is degraded when the sensor is operated in a low pressure regime (below about 100 Torr). This is due to that the signal strength across the gap decreasing as the pressure of the gas mixture therein decreases, resulting in a small signal to noise ratio and therefore affecting the accuracy and reliability of measurement.

There is a need, therefore, for a sensor that can operates in low pressure and/or high temperature environments in which conventional systems either do not provide usable data or would be damaged.

SUMMARY

In a CVD or ALD process, where the growth of crystals occurs by chemical reaction on the surface of the substrate, the process parameters must be controlled with particular care to ensure that the chemical reaction proceeds under the required conditions. Even small variations in process conditions can adversely affect device quality and production yield. Accordingly, there is a need for a concentration sensor that can be used at higher temperature, minimize noise while increasing total signal even at low pressures (below 100 Torr). Therefore providing information on the concentration of precursor and carrier gases that is more accurate.

According to embodiments, systems and methods are disclosed that provide for higher signal, lower noise, and/or a higher signal-to-noise ratio, for gas concentration sensors. Such sensors can be used in CVD or ALD systems, and can be used in a wider range of operating conditions than traditional sensors. The sensor can include a pair of transducers separated by a chamber in which the gas to be measured can be routed. Each transducer can further be coupled to a transformer that separates the transducers from the gas in the chamber and transforms the vibration of the transducers into acoustical data in the gas.

In embodiments, these improvements are achieved by using a metallic material or metal couplant, such as a solder, between a piezoelectric transducer and a transformer, to reduce acoustical mismatch between the layers of the overall system including transformer, couplant, and transducer. Reduced acoustical mismatch, in turn, reduces internal reflections. Fewer internal reflections both increases usable signal transmitted by the transformer to an adjacent gas, as well as reducing unwanted acoustical noise.

Furthermore, in some embodiments, a metallic material or metal couplant can be used to connect multiple layers, or leaves, of piezoelectric components together to form each transducer. This also has the effect of increasing the total amount of usable signal transmitted.

The metallic material or metal couplant can be capable of withstanding harsher operating conditions (such as high temperatures) that would destroy conventional couplants, while transmitting higher levels of acoustical signal due to the better acoustic match between the metallic material or metal couplant, typical ceramic piezoelectrics, and the metal (e.g., stainless steel) that makes up the bulk of the transformer.

In embodiments, additionally or alternatively to the improvements described above, a layer of polymer or other material having acoustical transmission properties between that of the metal body of a transducer and the gases to be measured can be disposed on the surface of the transformer. As such, internal reflections within the transformers are reduced, resulting in greater acoustical signal transmitted to the receiving transducer.

Additionally or alternatively, a pad of absorbent or highly acoustically attenuating material can be disposed between the brackets holding the transducer/transformer systems to an acoustic cell. In this way, acoustic transmission that would otherwise occur through the body of the acoustic cell, rather than through the gases to be measured is reduced. This has the effect of eliminating unwanted noise transmitted between the transducers.

The features described above can be used, alone or in combination, resulting in a sensor for gas concentration in a CVD or ALD system that is usable in a wider range of operating conditions such as relatively high temperature and low pressure compared to that used in conventional systems, while providing higher signal levels, lower unwanted noise levels, and/or a higher signal-to-noise ratio.

The above summary of the invention is not intended to describe each illustrated embodiment or every implementation of the present invention. The detailed description and claims that follow more particularly exemplify these embodiments.

BRIEF DESCRIPTION OF THE DRAWINGS

The disclosure can be more completely understood in consideration of the following description of various embodiments of the disclosure, in connection with the accompanying drawings, in which.

Figure 1:
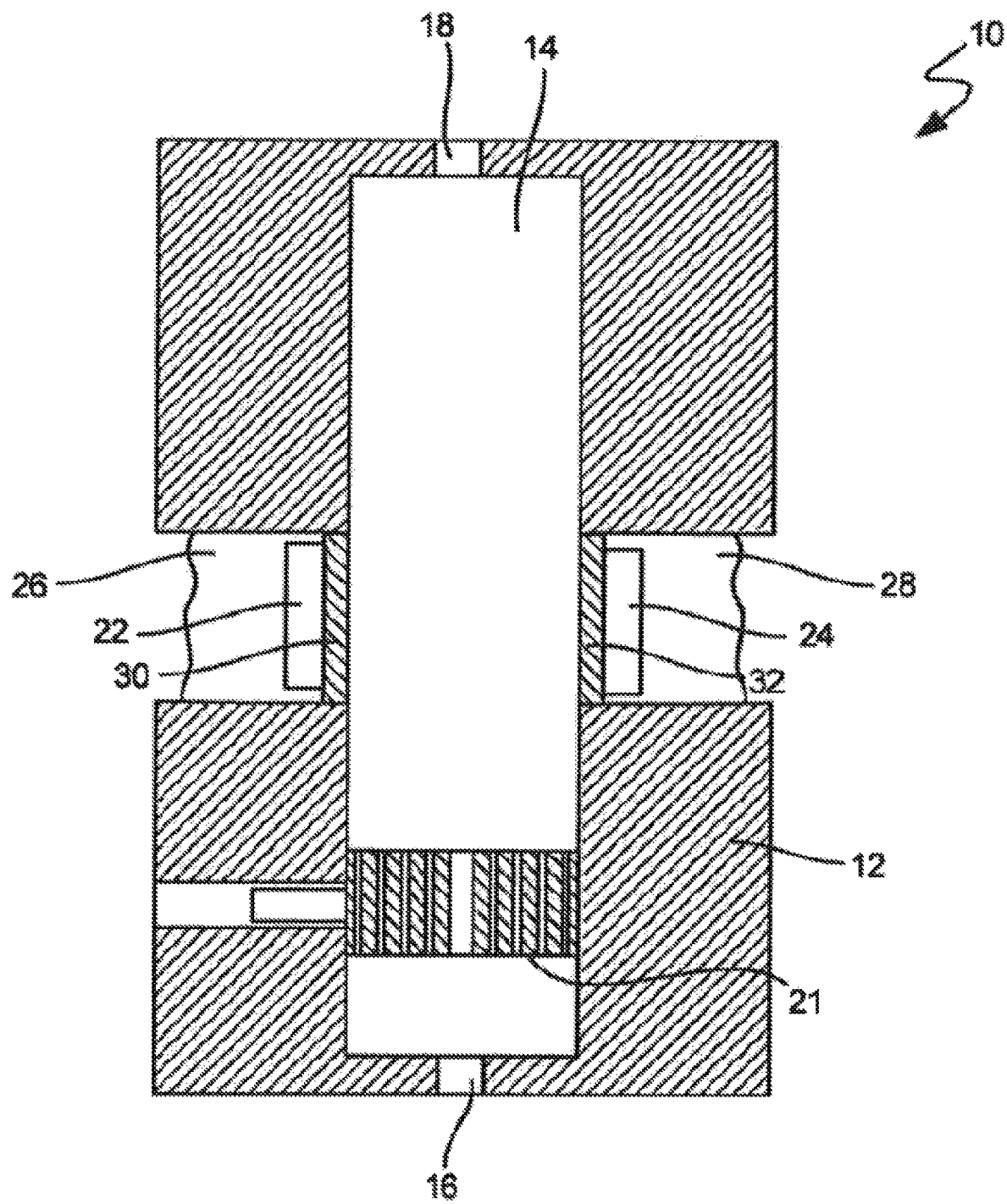
FIG. 1 is a cross-sectional view of a binary gas sensor, according to an embodiment.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DESCRIPTION OF THE EMBODIMENTS

In the embodiments described and claimed herein, the aforementioned problems of achieving high signal to noise ratio, even at low operating pressure and/or increased operating temperature, are resolved. More robust, accurate sensors capable of operating in a wider range of conditions are beneficial in that they can be used to enhance quality of the products made by CVD or ALD in a corresponding chamber, and are less prone to damage due to heat.

Some examples of pertinent conventional technology are described in U.S. Patent Application Publication No. 2012/0040097, U.S. Pat. Nos. 8,092,599, 8,021,487, U.S. Patent Application Publication No. 2007/0186853, U.S. Pat. Nos. 6,902,623, 6,506,252, and 6,492,625, the disclosures of which are incorporated by reference herein. Examples of inverted gas injection systems are described in U.S. Pat. No. 8,133,322, U.S. Patent Application Publication No. 2004/0175939, and U.S. Patent Application Publication No. 2004/0060518, the contents of which are hereby incorporated by reference herein. Examples of ALD systems are described in U.S. Pat. Nos. 9,145,608, 8,877,300, 8,758,512, 8,840,958, 9,236,467, 9,234,274, and 9,017,776, the contents of which are hereby incorporated herein by reference. These references provide some examples of terminology used herein.

Use of acoustic signal across a chamber containing the precursor gases involves signal processing to separate noise from signal. Sufficient levels of signal can be separated from the noise to generate an output indicative of the level of each precursor gas within the chamber. U.S. Pat. No. 6,279,379, which is incorporated by reference in its entirety, describes some such systems and methods.

FIG. 1 is a cross-sectional view of a binary gas sensor 10, according to a first embodiment. Binary gas sensor 10 includes acoustic cell 12, which defines the outer edge of a chamber 14. During operation of binary gas sensor 10, chamber 14 can be purged with the gas or gases that are to be delivered to a reactor housing (not shown) of a CVD or ALD system. Such gas(es) can be introduced at the inlet 16 to chamber 14, and expelled at the outlet 18 of chamber 14.

While in use, acoustic transmission through chamber 14 can be used to determine the speed of sound and overall acoustical transmission of the gas mixture that occupies chamber 14. Acoustic transmission is affected by pressure, temperature, and the composition and concentration of gases in chamber 14. Therefore, based on these data, it is possible to determine the concentrations of precursor and/or carrier gases present in chamber 14.

In the embodiment of binary gas sensor 10 shown in FIG. 1, temperature is measured by a sensor (not shown) at the acoustic cell 12. Uniform temperature between the gas(es) in the chamber 14 and acoustic cell 12 is maintained by thermally coupling the interior space defined by chamber 14 and diffuser 21, which is also thermally coupled to acoustic cell 12. In embodiments, heat or information corresponding to the level of heat within chamber can be transmitted to a temperature sensor—such as a thermometer, thermocouple, pyrometer, or another similar device or system—via a window or heat exchanger. In various alternate embodiments, a temperature sensor can be positioned within chamber 14 to measure temperature therein directly.

Acoustic transmission can be used, in conjunction with temperature data acquired by a temperature sensor, to determine a gas concentration within chamber 14. A first transducer 22, which can include a piezoelectric component, is configured to be driven with an electrical signal to generate an acoustic signal. The acoustic signal is transmitted across chamber 14 towards the second transducer 24. Once received at second transducer 24, the signal is converted back to electrical signal which can be analyzed, as discussed in more detail below. Furthermore, in embodiments, signal received at second transducer 24 re-transmitted back across chamber 14 towards first transducer 22. The time of flight of the signal through chamber 14, provides information regarding the concentrations of precursor gases within chamber 14, as described in detail in U.S. Pat. No. 6,279,379, previously incorporated by reference in its entirety.

First transducer 22 and second transducer 24 can be, for example, piezoelectric components. In some embodiments, first transducer 22 and second transducer 24 each comprise a single slab of piezoelectric material. In other embodiments, first transducer 22 and/or second transducer 24 can comprise multiple piezoelectric slabs, arranged in stacks extending away from chamber 14 (i.e., horizontally with respect to the layout shown in FIG. 1). In embodiments, the piezoelectric components that make up first transducer 22 and second transducer 24 can be arranged to vibrate primarily towards and away from chamber 14, such that acoustic signal is primarily routed directly across chamber 14.

First transducer 22 and second transducer 24 can be electrically coupled to a remote signal source (not shown), in embodiments, to provide the desired input signal. The remote signal source can be, for example, a processor, computer system, and/or voltage source that is configured to provide input electrical signal at a frequency range that will travel through the expected gas mixture in chamber 14, with a time of flight based on the concentration of precursor and/or carrier gases therein. First transducer 22 and second transducer 24 can also be electrically coupled to remote analytics device(s) or system(s) (also not shown) that receive electrical signal and can determine, based on the time of flight of the received signal, what concentration of precursor and/or carrier gases are present within chamber 14.

Acoustic data is carried between chamber 14 and first transducer 22 by transformer 30. Likewise, on the opposite side of chamber 14, acoustic data is carried between second transducer 24 and transformer 32. Transformers 30, 32 are arranged along chamber 14 to define sidewalls thereof. In conventional systems, transformers 30 and 32 are attached to transducers 22 and 24, respectively, with an adhesive or a resin such as an epoxy. The same adhesive or resin can also be employed between slabs of piezoelectric elements to bind them together and promote acoustic transmission, in conventional systems. In the embodiment shown in FIG. 1, transducer 22 is coupled to transformer 30 with a metallic material or metal couplant. For example, the metallic material or metal couplant can be a solder alloy.

Use of a metallic material or metal couplant rather than conventional epoxy or adhesive provides several advantages. These advantages are described below with respect to the first transducer 22, but it should be understood that these benefits apply equally to the second transducer 24, or any other transducer used in various alternative embodiments.

First, metallic material or metal couplant can be used in higher temperature environments than many polymeric or resin-based materials. In many cases, the deleterious effects of high temperature on the epoxy is not reversible, and once a binary gas sensor 10 is operated at a sufficiently high temperature the strength of the bonding created by epoxy or adhesive may be degraded.

Second, acoustic transmission through sufficiently thin layers of solder provides a desirably high level of acoustic data transfer as compared to conventional, epoxy-based systems. In embodiments, a solder layer of between about 25 µm (0.001 inches) and about 51 µm (0.002 inches), or more preferably approximately 38 µm (0.0015 inches), provides adequate adhesion and acoustic data transfer between an approximately 2.54 cm (1 inch) diameter, 4 mm thick piezoelectric transducer 22 and a corresponding stainless steel transformer 30 operating at about 500 kHz. The thickness of these components depends on the operating frequency of the system, and in embodiments where the operating frequency is lower the thickness of each component can be greater. For example, a system configured to operate at 1 MHz could have a piezoelectric transducer 22 having a 2 mm thickness, whereas a system configured to operate at 250 kHz could have a piezoelectric transducer 22 having an 8 mm thickness.

In embodiments, the thickness of the solder layer can be thick enough such that any mismatch between the coefficients of thermal expansion (CTE) of the solder layer and the adjacent components (whether piezoelectric, metallic, or both) does not cause sufficient stress to result in mechanical failure. Conversely, the thickness of the solder layer may be thin enough to prevent standing internal reflections, which can be avoided by limiting the thickness of the solder layer to about one quarter of the wavelength of the acoustical signal passing through the layer or less. In embodiments, both of these desired thickness properties can be achieved by using a solder layer having a thickness of between about 25-50 µm.

In fact, acoustic data transmission may be improved compared to epoxy or adhesive, because of reduced acoustic mismatch. Transducer 22 is often a ceramic piezoelectric component, and transformer 30 can include a metal such as stainless steel (SS). Acoustic waves transmit or reflect at the interface between any two materials based on the level of acoustic impedance mismatch between them; the higher the mismatch, the more of that wave will be reflected rather than transmitted. Therefore, it is desirable to identify a joining material that has a low acoustic impedance mismatch with both the ceramic of transducer 22 and the metal of transformer 30. Solder metal blends often have acoustic properties more similar to those of transducer 22 and transformer 30 than acoustic properties of epoxy resins do, and therefore less acoustic energy is reflected at each interface. Not only does this reduce the amount of power that must be delivered by the transducer 22, but it also reduces noise in the signal generated by piezoelectric transducer 22 by reducing the amplitude of reflected acoustic waves.

Third, metal solder can prevent cleaving between layers, and provide better adhesion and less stress on adjacent components, by more closely matching the CTE of the various materials within binary gas sensor 10. In general, at the interface between two layers having different CTE, deviations from a "zero strain" reference temperature causes mechanical stress and strain between those layers. When the binary gas sensor 10 deviates from the zero strain temperature, mismatch between the CTE of mechanically bonded layers causes mechanical deformation, leading to stress and strain between components that can result in cracking, delamination, or other mechanical failures. One example of such mechanically bonding is the interface between transducer 22 and transformer 30.

In one embodiment, transducer 22 comprises a piezoelectric ceramic having a CTE of about $4 \times 10^{-6}$/deg-C, transformer 30 comprises a steel alloy having a CTE of about $1.6 \times 10^{-5}$/deg-C, and a tin-silver solder mechanically and acoustically coupling them has a CTE of about $2.2 \times 10^{-5}$/deg-C. Meanwhile, epoxy resins often have a CTE of about $4.5 \times 10^{-5}$/deg-C to about $6.5 \times 10^{-5}$/deg-C. The exact CTE of various epoxies, piezoelectric ceramics, and steel alloys can vary, but in general tin-silver alloys referred to previously or similar materials will have a CTE closer to that of both piezoelectric ceramics as well as steel alloys, as compared to epoxy resins or adhesives.

Transformers 30 and 32 can comprise multiple materials, in embodiments. In one embodiment, transformers 30 and 32 include a stainless steel portion adjacent to transducers 22 and 24, respectively, and a layer of polymeric material adjacent to chamber 14. These materials allow for closer matching of the acoustical properties between transformers 30 and 32 and the precursor gases typically used in chamber 14. For example, transformers 30 and 32 can be comprised mainly of stainless steel, with a thin layer of KAPTON® polyimide material disposed adjacent chamber 14, in embodiments. The thin layer of KAPTON® or other polymeric material can reduce a dropoff in signal present in some conventional systems, in which there is poor transmission of acoustic signal from stainless steel transformers to the precursor gases due to acoustic impedance mismatch, causing reflection (increasing signal loss) and refraction (potentially increasing signal noise and resulting in signal loss) at the transformer/chamber interface.

In general, the transducer 22 is excited at the frequency close to its natural resonant frequency in order to generate a maximum acoustic energy. As result of physical resonance, the transducer tends to oscillate (or ring) after excited signal is removed. The extend ringing generates unwanted signal which could affect the main signal. For this reason, first transducer 22 and second transducer 24 are mechanically attached to damper 26 and 28, respectively. The dampener material can be selected such that they have a high acoustic attenuation coefficient and a coefficient of thermal expansion (CTE) that is close to or similar to piezoelectric materials. Dampener materials with these characteristics can attenuate unwanted acoustical signals as well as suppress the ringing. Examples of dampener materials include epoxy, polymeric materials, carbon-carbon composites (for example, carbon fiber composites), and/or combinations thereof, and the like.

The embodiment of binary gas sensor 10 shown in FIG. 1 solves many of the deficiencies of conventional systems. Through the elimination of epoxy at the transducers and transformers, the operating temperature range is increased, reducing or eliminating the necessity to operate a corresponding CVD or ALD system "blind." Through the use of metal solder to couple the same components, acoustic transmission is increased, and CTE mismatch is reduced, resulting in reduced potential for a variety of mechanical failure modes. Through the use of a transformer 30 or 32 that comprises multiple materials, internal reflection and refraction of acoustic signal into chamber 14 can be reduced as compared to conventional systems. In sum, binary gas sensor 10 can provide data relating to the relative concentrations of precursor and/or carrier gases within chamber 14 at a wider range of temperatures and pressures, and increases the quantity of usable transmitted signal while reducing potential sources for noise.

Figure 2A:
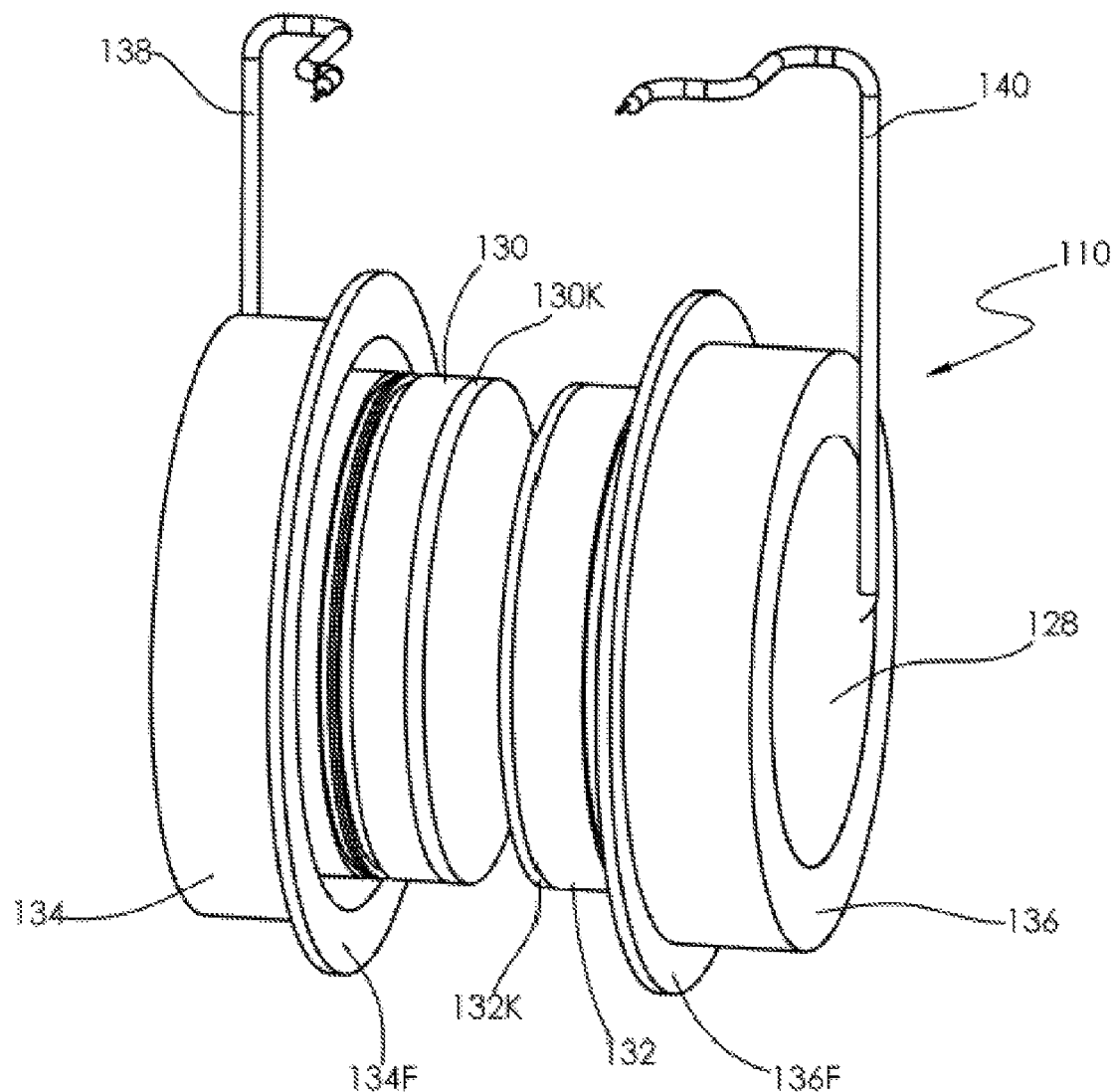
FIG. 2A is a perspective view of a pair of acoustical detection and emission elements, according to an embodiment.

A similar system to that previously described with respect to FIG. 1 is shown in exploded view in FIG. 2A. The embodiment of binary gas sensor 110 shown in FIG. 2 includes many components similar to those previously described with respect to FIG. 1. In general, throughout this disclosure, embodiments having like parts are described with like reference numerals, iterated by factors of 100. So, for example, binary gas sensor 110 includes first transducer 122, second transducer 124, first dampener 126, second dampener 128, and transformers 130 and 132, which are substantially similar to first transducer 22, second transducer 24, first dampener 26, second dampener 28, and transformers 30 and 32, respectively, as depicted in FIG. 1.

In addition to the components previously described, FIG. 2A shows housing 134 having flange 134F. Housing 134 surrounds first dampener 126 and flange 134F is a portion of housing 134 that can be coupled to an acoustic cell (e.g., acoustic cell 12 previously described with respect to FIG. 1). In embodiments, housing 134 can be made of a material such as a metal such that screws, bolts, threads, or other fasteners can be used to removably mechanically couple housing 134 an adjacent component such as an acoustic cell.

Housing 134 is configured to hold the other components that form one half of the binary gas sensor 110. As shown in FIG. 2, housing 134 holds and partially surrounds first dampener 126. First dampener 126 provides a mechanical damping and suppresses any ringing mode which is generated from the first transducer 122, as previously described. First transformer 130 is disposed on the opposite side of first transducer 122 from first dampener 126. In this arrangement, first transducer is mechanically held by housing 134, but acoustic signal created by first transducer 122 can easily travel to first transformer 130.

Housing 136 and flange 136F similarly mechanically hold second transducer 124, and facilitate transmission of acoustic signal from second transducer 124 to second transformer 132 while suppressing acoustic energy and reducing the ringing through second dampener 128. In embodiments, first transducer 122, first dampener 126, first transformer 130, and housing 134 form a combined structure that is similar to second transducer 124, second dampener 128, second transformer 132, and housing 136, though the exact geometry of the transformer and transducer can vary as shown in the following figures. In embodiments, first transducer 122, first dampener 126, first transformer 130, and housing 134 can form an emitter and second transducer 124, second dampener 128, second transformer 132, and housing 136 can form a receiver, which may have different physical dimensions or specifications depending on the signals expected to be sent or received, respectively, during normal usage.

In the embodiment shown in FIG. 2A, leads 138 and 140 are electrically coupled to first transducer 122 and second transducer 124 (not shown), respectively. As previously described with respect to FIG. 1, electrical signal can be applied to first transducer 122 to generate acoustic signal, and contrariwise acoustic signal received at the second transducer 124 results in electrical signal output. Leads 138 and 140 can be used to route such electrical signals both to and from transducers 122 and 124. In the embodiment shown in FIG. 2, leads 138 and 140 pass through apertures formed in housings 134 and 136, and are surrounded by first dampener 126 (not shown) and second dampener 128, respectively, en route to transducers 122 and 124.

Figure 2B:
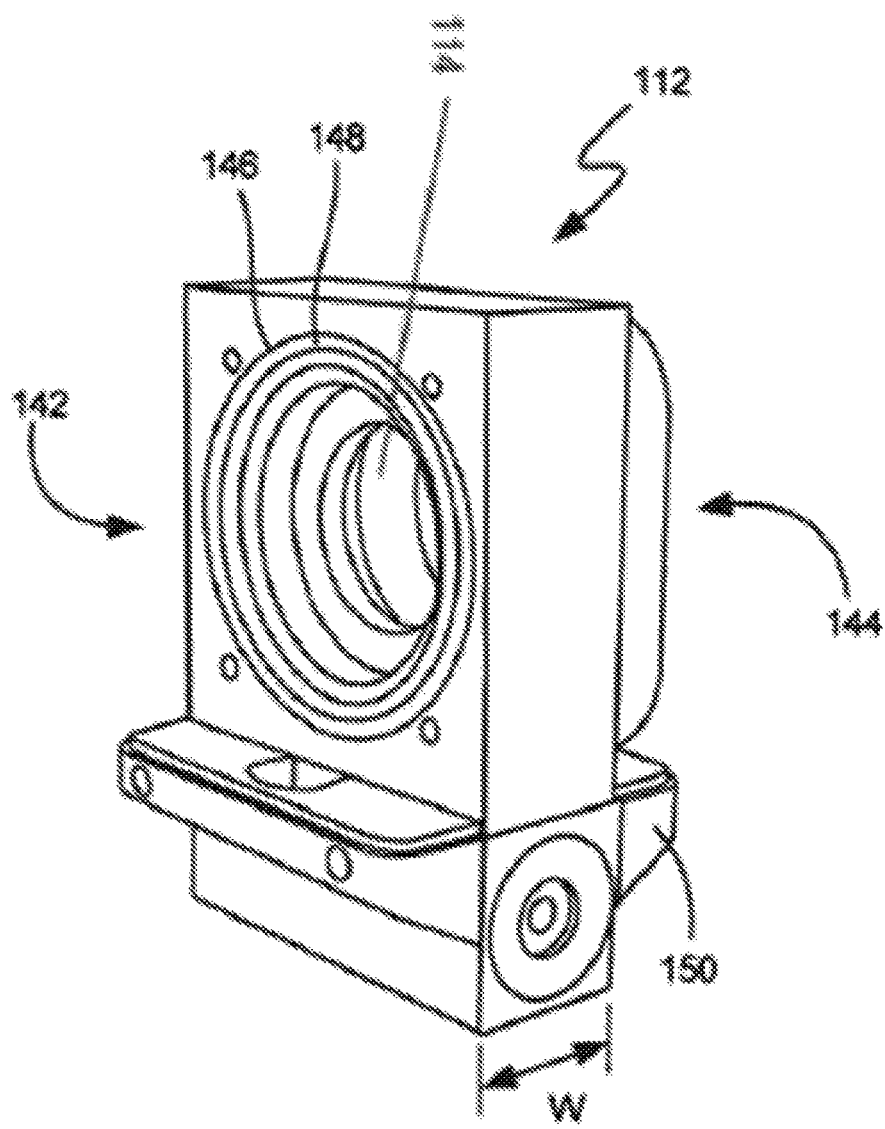
FIG. 2B is a perspective view of an acoustic cell, according to an embodiment.

FIG. 2B depicts an acoustic cell 112 that can be used to measure the concentration of various precursor gases. Acoustic cell 112 of FIG. 2B can be used with the gas sensor 110 of FIG. 2A. Acoustic cell 112 includes first side 142 and second side 144. Each side (142, 144) is configured to receive an acoustic transmitter/receiver such as those described previously with respect to FIG. 2A. Acoustic cell 112 can be used with such transmitters/receivers to detect overall transmitted acoustic signal within a range of frequencies. Based on the time of flight of acoustic signal between the sides (142, 144), the concentrations of various precursor and/or purge gases can be calculated. Because acoustic signal is dependent on the distance between an emitter and receiver, acoustic cell 112 is configured such that the width w between the two sides (142, 144) is a known constant.

In the perspective view shown in FIG. 2B, the features of first side 142 are shown. It should be understood that, although not depicted in this perspective view, identical or symmetrical structures are also included on second side 144 of acoustic cell 112. For example, first side 142 includes landing 146 and o-ring 148. Second side 144 also includes similar structures, in embodiments.

The structures previously described with respect to FIG. 2A can be used in conjunction with acoustic cell 112. As noted with respect to FIG. 2A, the transducers 122 and 124 can be housed in two halves of an overall sensor system. Each half can be mounted to one side of acoustic cell 112 as shown in FIG. 2B. For example, flange 134F can be arranged at landing 146. As a result, transformer 130 and transformer 132 previously shown with respect to FIG. 2A are kept at a well defined distance based on width w of acoustic cell 112, and the area defined by transformers 130 and 132, as well as acoustic cell 112, defines a chamber (e.g., chamber 14 of FIG. 1).

Acoustic signal is desirably transmitted through chamber 114, and it is generally undesirable for acoustic signal to travel between first transducer 122 and second transducer 124 via any other route. For this reason, first transducer 122 and second transducer 124 are acoustically isolated from acoustic cell 112 using the O-ring 148. The O-ring can be made of any material which has lower acoustic impedance comparing to the flange 134 and also can provide a hermetic seal between acoustic cell 112 and housing 134. In embodiments, the O-ring 148 is made of Viton® fluoroelastomer.

As shown in FIG. 2B, acoustic cell 112 further includes ballast 150. Ballast 150 can be used, in embodiments, to increase the thermal heat capacity of acoustic cell 112. By routing precursor gases through the body of acoustic cell 112, and maintaining sufficient levels of thermal transfer between the precursor gases and acoustic cell 112, temperature measurement of the acoustic cell 112 can be used to provide a measurement of the temperature of the precursor gases without necessitating direct temperature measurements within the chamber 114. Ballast 150 increases the thermal heat capacity of acoustic cell 112 to avoid swings in temperature in the precursor gases, and improves the precision of such temperature measurements.

Figure 2C:
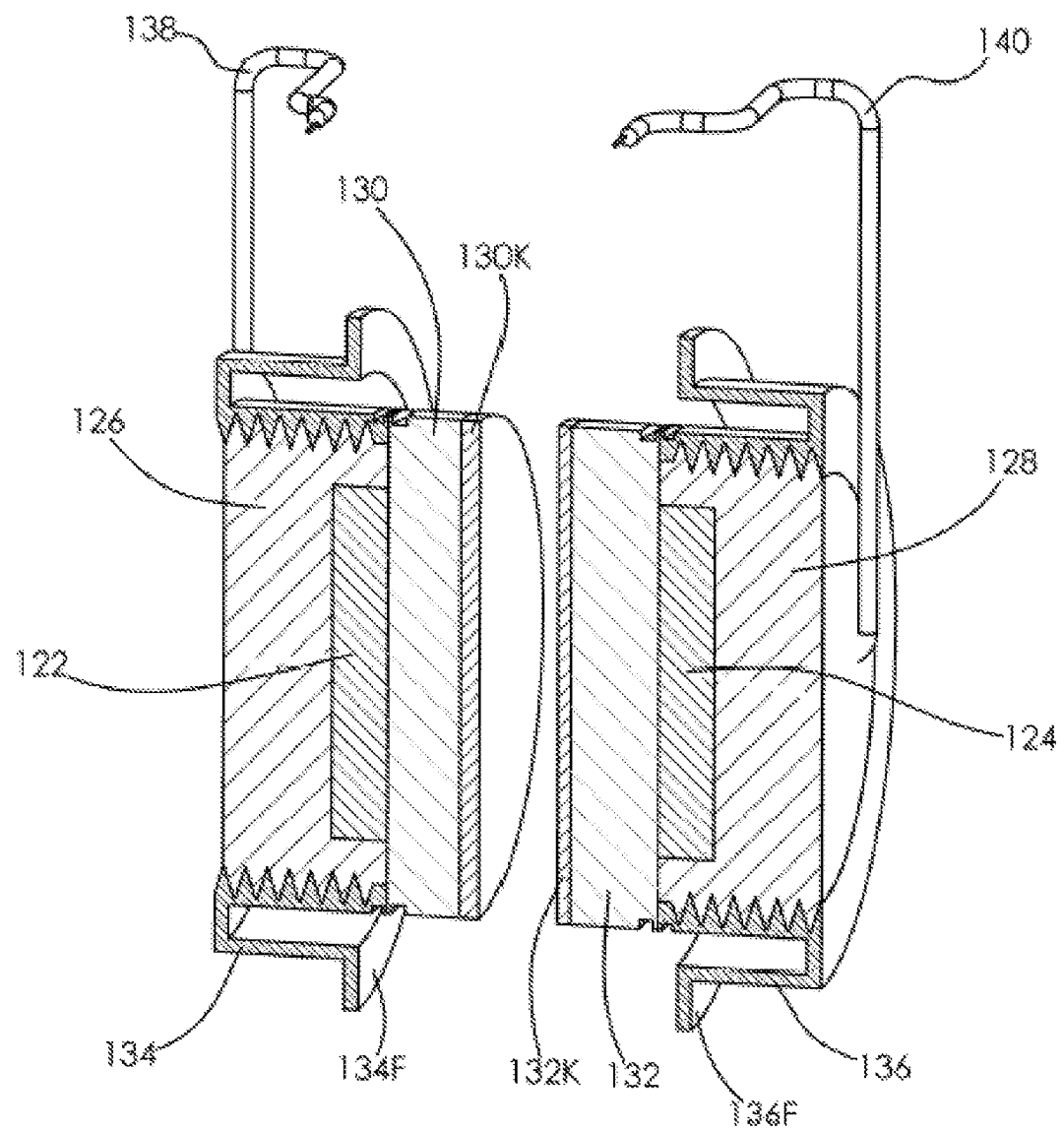
FIG. 2C is a cross-sectional view of the acoustic cell of FIG. 2A, according to an embodiment.

FIG. 2C shows a cross-section of the binary gas sensor 110 of FIG. 2A, using the same reference numbers. 122 and 124 are the first and second transducers.

Figure 3A:
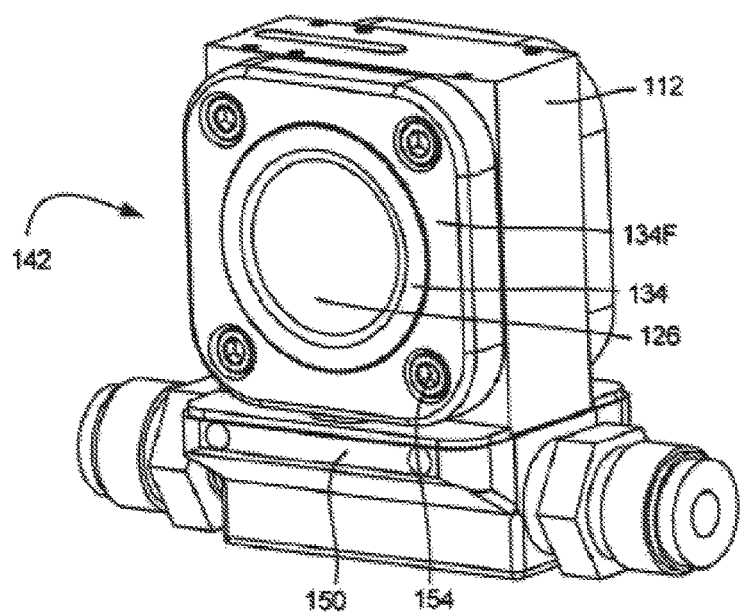
FIGS. 3A and 3B depict perspective views of opposite sides of an acoustic cell having detection/emission elements mounted thereto, according to an embodiment.
Figure 3B:
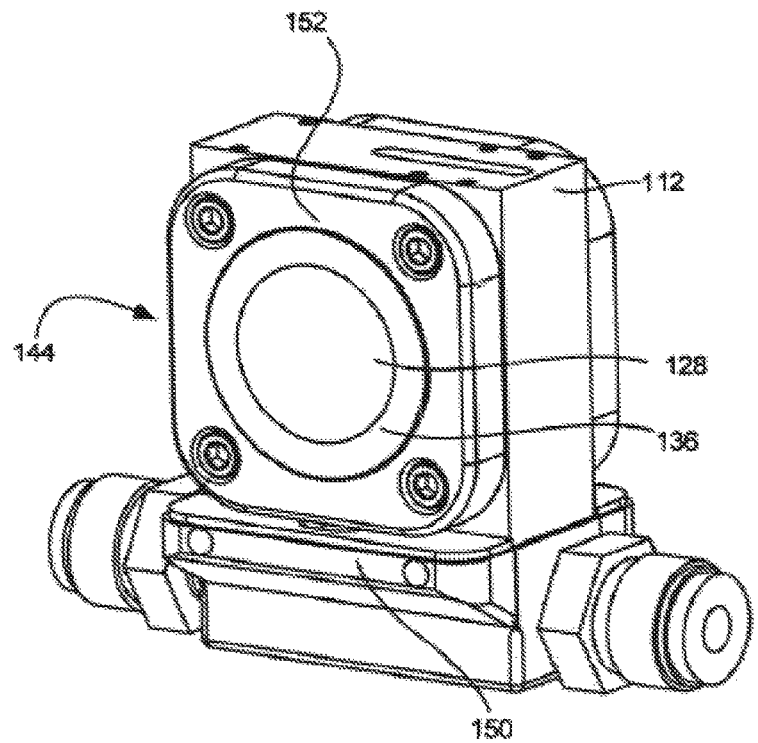

FIGS. 3A and 3B are partial perspective views of structures mounted to acoustic cell 112. The views depicted in FIGS. 3A and 3B are from two opposite perspectives, showing acoustic cell 112 from the first side 142 in FIG. 3A, and the second side 144 in FIG. 3B.

FIG. 3A depicts a portion of acoustic cell 112, upon which is mounted housing 134 having flange 134F (not shown). Visible through the back of housing 134 is first dampener 126. By positioning housing 134 on first side 142 of acoustic cell 112, acoustic signal can be provided to the chamber (e.g., chamber 14).

FIG. 3B depicts similar structures to those shown previously with respect to FIG. 3A, applied to second side 144 of acoustic cell 112. As previously described with respect to FIGS. 1, 2A, 2B, and 2C corresponding counterparts to the structures shown in FIG. 3A are depicted. In particular, FIG. 3B depicts second housing 136, having flange 136F, and second dampener 128. Furthermore, FIG. 3B depicts bracket 152. Bracket 152 holds housing 136 to second side 144 of acoustic cell 112, and can be used to adjust the pitch or angle of structures mounted to second side 144.

It may be desirable in embodiments to provide an attachment mechanism that, like the screwed-in embodiment shown in FIGS. 3A and 3B, is removable. In embodiments, it may also be desirable to provide an attachment mechanism that provides consistent and uniform distance between acoustic cell 112 and housings 134/136. In this way, the distance and angle between transducers 122 and 124 (FIGS. 2A and 2B) can precisely set and maintained.

Figure 4:
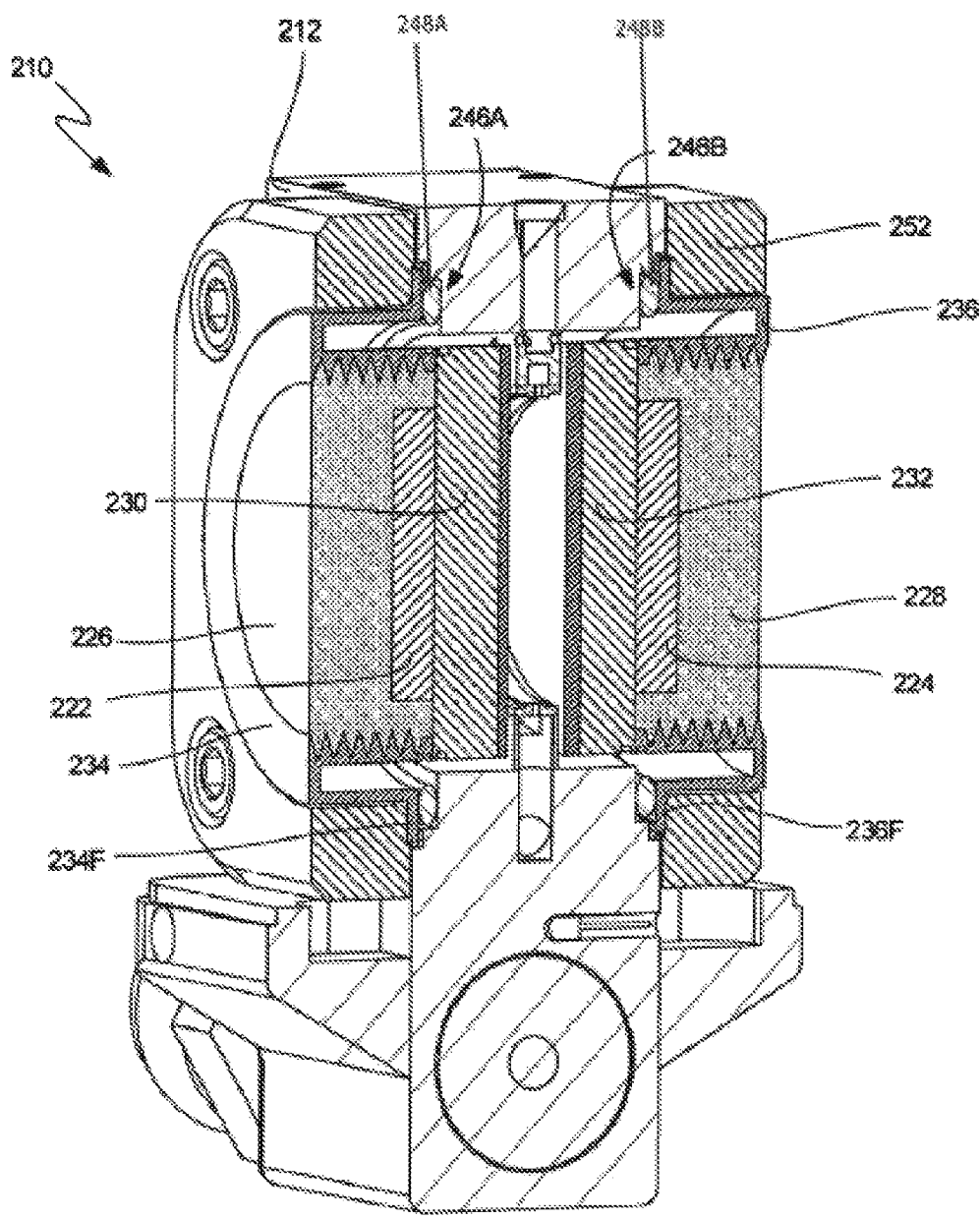
FIG. 4 is a cross-sectional perspective view of an acoustic cell having detection/emission elements mounted thereto, according to an embodiment.

FIG. 4 is a partial cross-sectional view of an assembled binary gas sensor 210, according to an embodiment. In the embodiment shown in FIG. 4, first transducer 222 is configured to provide an acoustic data output, and and second transducer 224 is configured to receive the acoustic data. First and second dampeners 226 and 228 provides mechanical damping and reduces the signal ringing. Each structure comprising a transducer, a dampener, and a transformer (e.g., first transducer 222, first dampener 226, and first transformer 230; or second transducer 224, second dampener 228, and second transformer 232) is contained by a housing (e.g., first housing 234; or second housing 236, respectively) having a flange (e.g., flange 234F; or flange 236F, respectively). These structures are spaced apart by a distance defined by the contours of acoustic cell 212, which they are landed to O-rings 248A, 248B. In embodiments, one or both of the structures can be either permanently or removably attached to acoustic cell 212. The components on each side of acoustic cell 212 are held thereto by a bracket that can be bolted or otherwise affixed thereto (e.g., bracket 252 holds housing 236 to acoustic cell 212).

As described with respect to previous embodiments, first transducer 222 can be coupled to first transformer 230 via a metallic material or metal solder. Such coupling leads to higher rates of acoustic data transmission, and lower reflection and refraction of acoustic signal, as compared to epoxy resin or adhesive coupling. Furthermore, use of metal between first transducer 222 and first transformer 230 functions at relatively higher temperatures as compared to epoxy or adhesive, without losing fidelity or being damaged.

Figure 5A:
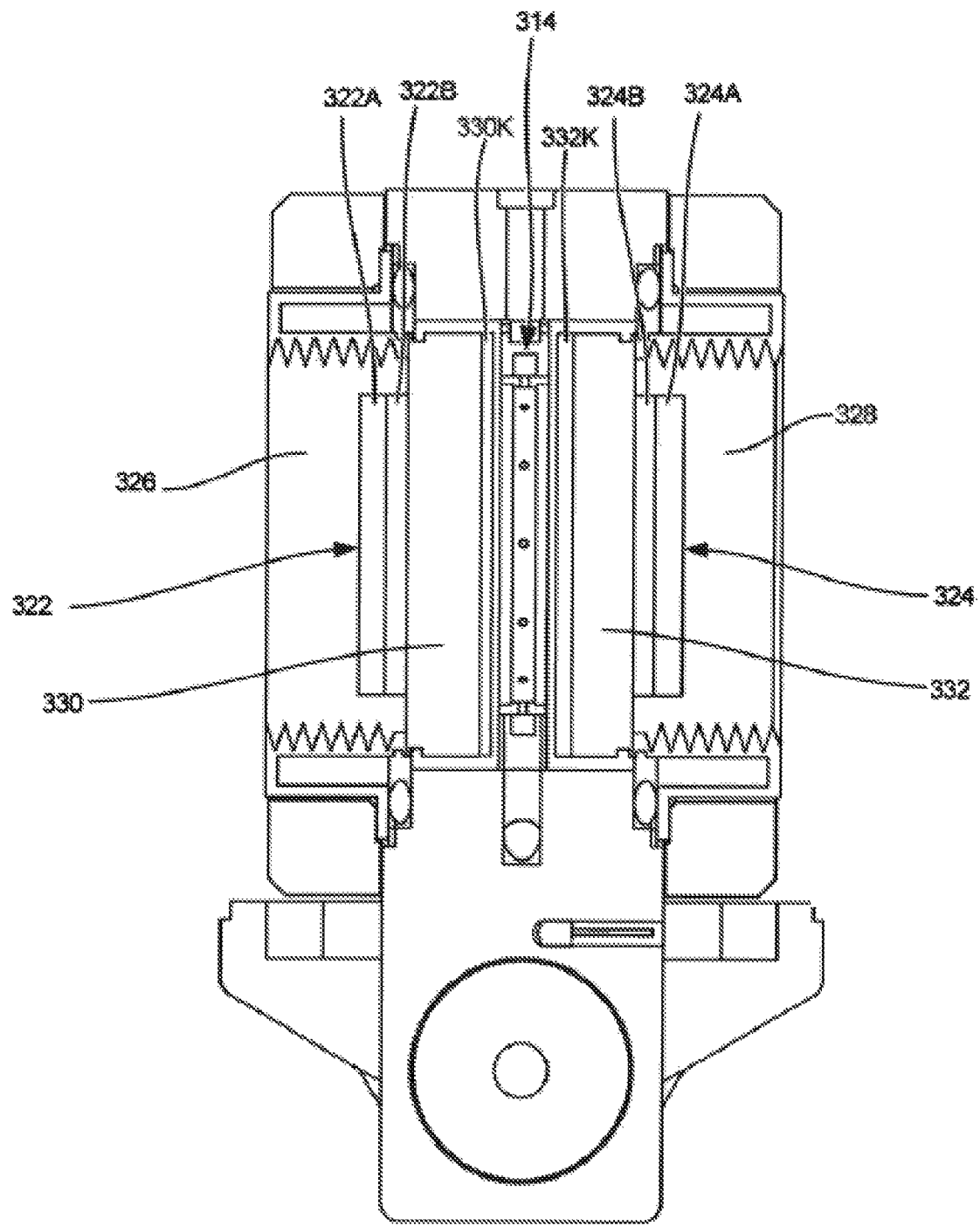
FIG. 5A is a cross-sectional perspective view of an acoustic cell having detection/emission elements mounted thereto, and wherein each of the detection/emission elements has a bisected piezoelectric transducer, according to an embodiment.
Figure 5B:
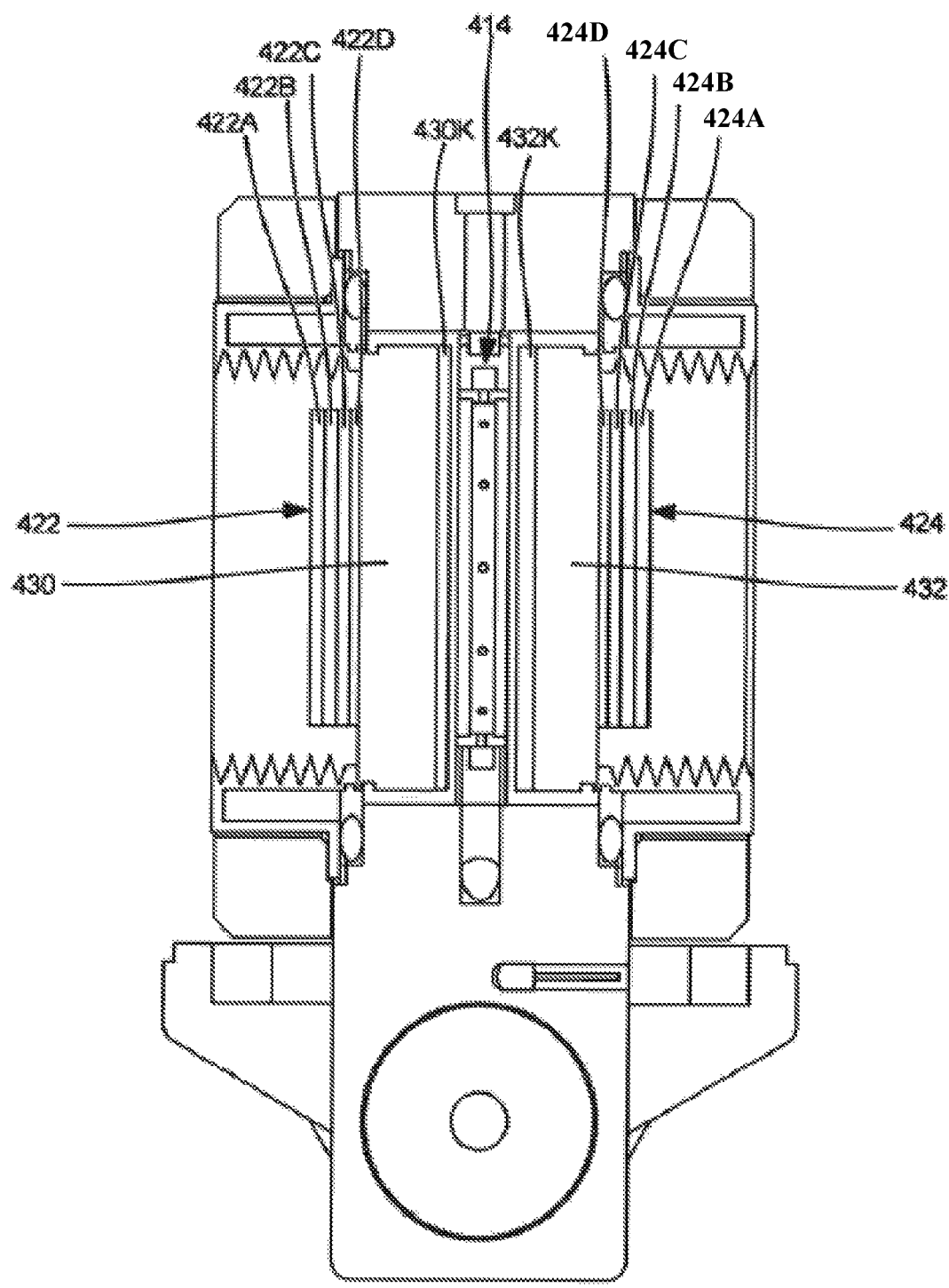
FIG. 5B is a cross-sectional perspective view of an acoustic cell having detection/emission elements mounted thereto, and wherein each of the detection/emission elements has a piezoelectric transducer made of four leaves, according to an embodiment.

FIGS. 5A and 5B depict alternative embodiments in which first transducer 322 and second transducer 324 comprise multiple sub-components. In particular, as shown in FIG. 5A, first transducer 322 comprises first sub-transducer 322A and second sub-transducer 322B. Likewise, second transducer 324 comprises first sub-transducer 324A and second sub-transducer 324B. Each first sub-transducer (322A, 324A) is arranged adjacent to its respective dampener (326, 328) while each second sub-transducer (322B, 324B) is arranged adjacent to chamber 314. It can be beneficial in embodiments to add even more sub-transducers. For example, as shown in FIG. 5B, first transducer 422 comprises first, second, third, and fourth sub-transducers 422A, 422B, 422C, and 422D; likewise, second transducer 424 comprises first, second, third, and fourth sub-transducers 424A, 424B, 424C, and 424D. Each sub-transducer can be narrower than the single transducers (22, 122, 222, 322) shown in previous embodiments, such that the overall thickness remains the same even where multiple sub-transducers are used. For example, the thickness of transducers 22, 122, 222, 322, and 422 can all be 4 mm. Thus, in the embodiment shown in FIG. 5A, the first sub-transducer 322A and second sub-transducer 322B can each be 2 mm thick. In order to achieve the same 4 mm thickness in the embodiment shown in FIG. 5B, each sub-transducer 322A, 322B, 322C, and 322D can be 1 mm thick. The thickness of solder or braze between the sub-transducers, in various embodiments, can be about 25-50 μm, for example, and in embodiments the combined thickness of the sub-transducers and the solder layers therebetween can be about 4 mm. In alternative embodiments, where a desired signal level is relatively lower, the thickness of each transducer can be relatively smaller, such as between about 1 mm and about 3 mm. In other embodiments in which a relatively large signal and/or high sensitivity is desired, each transducer can be thicker, for example between about 4 mm and about 7 mm.

As shown in FIGS. 5A and 5B, the transformers associated with the first side and the second side can be asymmetrical. In particular, as shown in FIG. 5A, first transformer 330 is thicker than second transformer 332; likewise, as shown in FIG. 5B, first transformer 430 is thicker than second transformer 432. In these embodiments, the first side (i.e., the side containing first transformers 330 and 430, respectively) is used for signal transmission, while the second side (i.e., the side containing second transformers 332 and 430, respectively) is used for receiving signal. A thicker transformer (330, 430) is used for the transmitting side than the transformer (332, 432) at the receiving side, to obtain a desired type of frequency response function of the sensor, improve signal processing, and improve accuracy of time of flight measurement and calculation of concentration of the gases.

In one embodiment, for example, first transformer 330 can have a thickness of between about 0.5 cm (0.197 inches) to about 0.55 cm (0.217 inches), and in one embodiment the thickness of first transformer 330 can be about 0.523 cm (0.206 inches). In embodiments, second transformer 332 can have a thickness of between about 0.6 cm (0.236 inches) and about 0.65 cm (0.256 inches), and in one embodiment the thickness of second transformer 332 can be about 0.630 cm (0.248 inches). Transformers 330, 332 can have various alternative thicknesses depending on the size and number of the transducers 322, 324, and the amount of acoustic signal transmitted and received. In the embodiments described above, for example, first transducer 322 and second transducer 324 can have a thickness of between about 0.381 cm (0.15 inches) and about 0.533 cm (0.21 inches). In general, each sub-transducer 322A, 322B, 322C, and 322D can be driven using a maximum voltage (e.g., 10 volts) which produces a set quantity of acoustic data based on the size and shape of each sub-transducer 322A, 322B, 322C, and 322D. Therefore, a larger transducer 322 or one including a greater number of sub-transducers 322A, 322B, 322C, and 322D can be paired with a thicker or larger transformer 330, and vice versa.

Additionally, FIG. 5A shows coating layers 330K and 332K. In some embodiments, as previously described, coating layers 330K and 332K comprise a material having acoustical properties that are between those of the bulk of transformers 330 and 332, and those of the fluid in chamber 314. For example, in one embodiment each of coating layers 330K and 332K can comprise a polyimide such as KAPTON®.

Figure 5C:
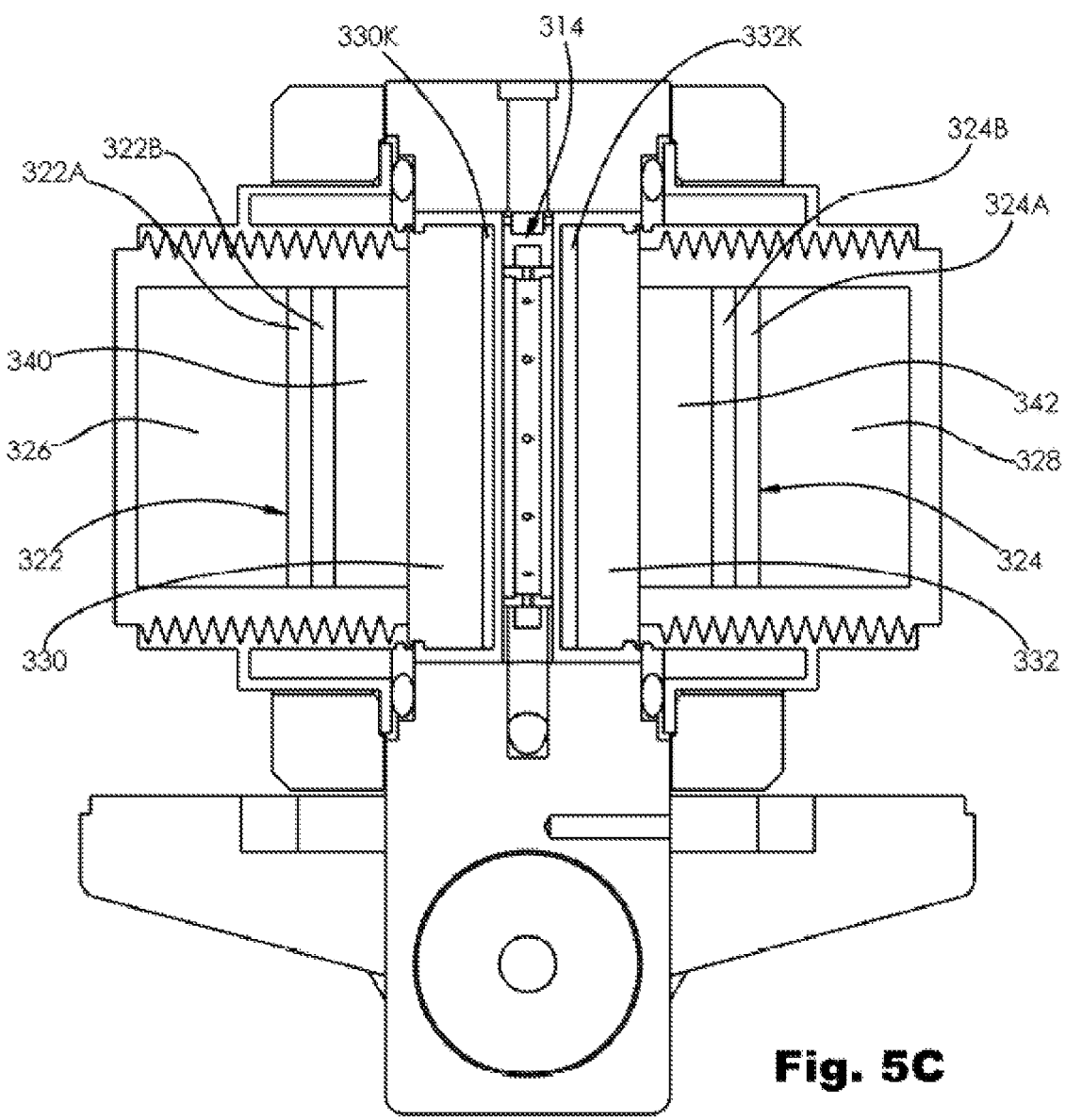
FIG. 5C is a cross-sectional perspective view of an acoustic cell having detection/emission elements mounted thereto, and wherein each of the detection/emission elements has a bisected piezoelectric transducer, according to an embodiment.

FIG. 5C depicts an alternative embodiment of that which is shown in FIG. 5A. Therein, FIG. 5C provides interlayers 340 and 342 which are placed between sub-transducer 332B and first transformer 330 and sub-transducer 324B and second transformer 332, respectively, for the embodiment in FIG. 5A (where the element numbers in FIG. 5C have the same meaning as those described for FIG. 5A herein). Interlayers 340 and 342 reduce the thermal expansion mismatch between the materials that make up the sub-transducer and the respective first and second transformer. The materials used for interlayers 340 and 342 generally have a coefficient of thermal expansion between about 17 ppm/° K and about 1.1 ppm/° K, more preferably between about 10 ppm/° K and about 1.1 ppm/° K. Examples of materials for interlayers 340 and 342 include titanium, rhenium, molybdenum, tantalum, Invar® (nickel-iron alloys), Kovar® (nickel-cobalt-iron alloys), their alloys, and the like.

Interlayers 340 and 342 can also be used other embodiments, such as that shown in FIG. 5B. Interlayers 340 and 342 can be placed in the embodiment shown in FIG. 5B between sub-transducer 422D and first transformer 430 as well as between sub-transducer 424D and second transformer 432.

Interlayers 340 and 342 can have thickness of between about 2 mm to about 12 mm, in embodiments.

Figure 6:
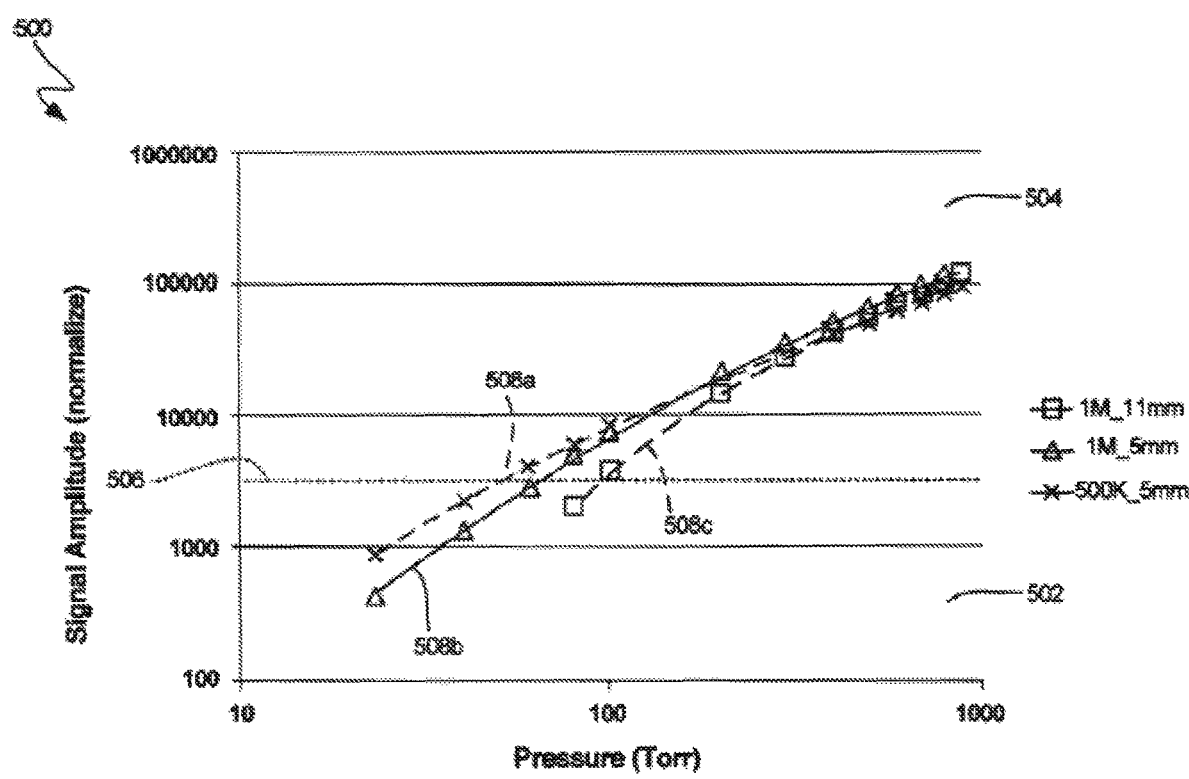
FIG. 6 is a chart depicting signal as a function of pressure and sensor geometry.

FIG. 6 is a chart of signal amplitude as a function of pressure in a chamber. As shown in FIG. 6, signal amplitude increases with increasing pressure in the chamber. In a first region 502, the signal amplitude is too low to distinguish signal from noise. In a second region 504, signal can be detected and analyzed as previously described with respect to FIG. 6 in order to ascertain a concentration of one or more precursor gases in chamber 414, or a ratio of precursor gas to carrier gas in chamber 414. Separating these two regions is cutoff 506. Signals 508a, 508b, and 508c correspond to different signal measurements.

The equation by which the concentration of precursor gas in the chamber 414 is calculated is:

$$\frac{L}{TOF} = C = \sqrt{\frac{\gamma z RT}{M}}$$

where L is the distance between the transducers, TOF is the time of flight of the signal, C is the speed of sound in the mixture, T is the temperature in the chamber, R is the ideal gas constant, z is the compressibility factor, γ is the specific heat ratio, and M is the molecular weight of the gas mixture.

In general, it is desirable that the signals 508a, 508b, 508c be located as much as possible within the second region 504, where usable signal can be gathered. The embodiments described herein provide higher signal and lower noise to generate more usable data.

First, there is a higher level of signal at each pressure, due to the metallic/solder bonds between transducer and transformer, and between the sub-components of multi-component transducers. This higher signal effectively moves the signals 508a, 508b, 508c to the left on the chart shown in FIG. 6.

Second, use of multi-layer piezoelectric components as transducers results in both higher signal and higher noise levels. This has the effect of shifting the signals 508a, 508b, and 508c to the left, and moving cutoff 506 up, with respect to the charge shown in FIG. 6.

Third, as will be described with respect to FIG. 7, the position of cutoff 506 can be lowered with respect to the chart shown in FIG. 6, by reducing the quantity of noise that is transferred through any other path than through the chamber of the acoustic cell.

The net effect of these three improvements over conventional systems is that there is a higher overall signal, and higher signal-to-noise ratio, permitting precision in precursor gas concentration measurement at lower pressure than was previously possible. In addition, as previously described, the resulting system is operable at higher temperature because it need not contain epoxy, and the system is therefore operable in a wider range of operating conditions.

As shown in FIG. 6, the slope of the signal loss as a function of decreased pressure is affected by signal frequency. As shown by the line marked with "X"s, signal dropoff at low pressure is relatively shallow for 500 kHz signal whereas, as shown by the line marked with "☐"s, signal dropoff is relatively steeper at low pressure for 1 MHz signal. Therefore, in order to facilitate use of the pressure sensors described herein at low pressure, systems may be driven at signal frequencies of 500 kHz or lower, such as 250 kHz in one embodiment. This reduces signal dropoff and permits use of the system at very low pressures. In one trial, 250 kHz signal was used to produce a sufficient signal-to-noise ratio at 10 Torr.

In embodiments, where lower frequency signal is used, the absolute and/or relative sizes of components used in the system are modified. For example, as previously described, a polymeric layer having different acoustical properties than the transformers can be arranged between the transformers and the chamber. In embodiments, the thickness of these polymeric layers can be a function of the wavelength of the signal passing therethrough, in order to reduce or prevent undesirable reflection and refraction. Similarly, in embodiments it is desirable to place a layer of a metal such as an Inconel alloy between the transformers and the chamber, either adjacent to the transformer itself or adjacent to the polymeric coating. In order to prevent reflection or refraction, it can be beneficial to apply a coating of no more than ¼ wavelength of the signal. Thus, with lower signal frequency, the coating of polymer and/or metal coatings can be modified in an inversely proportional relationship.

Figure 7:
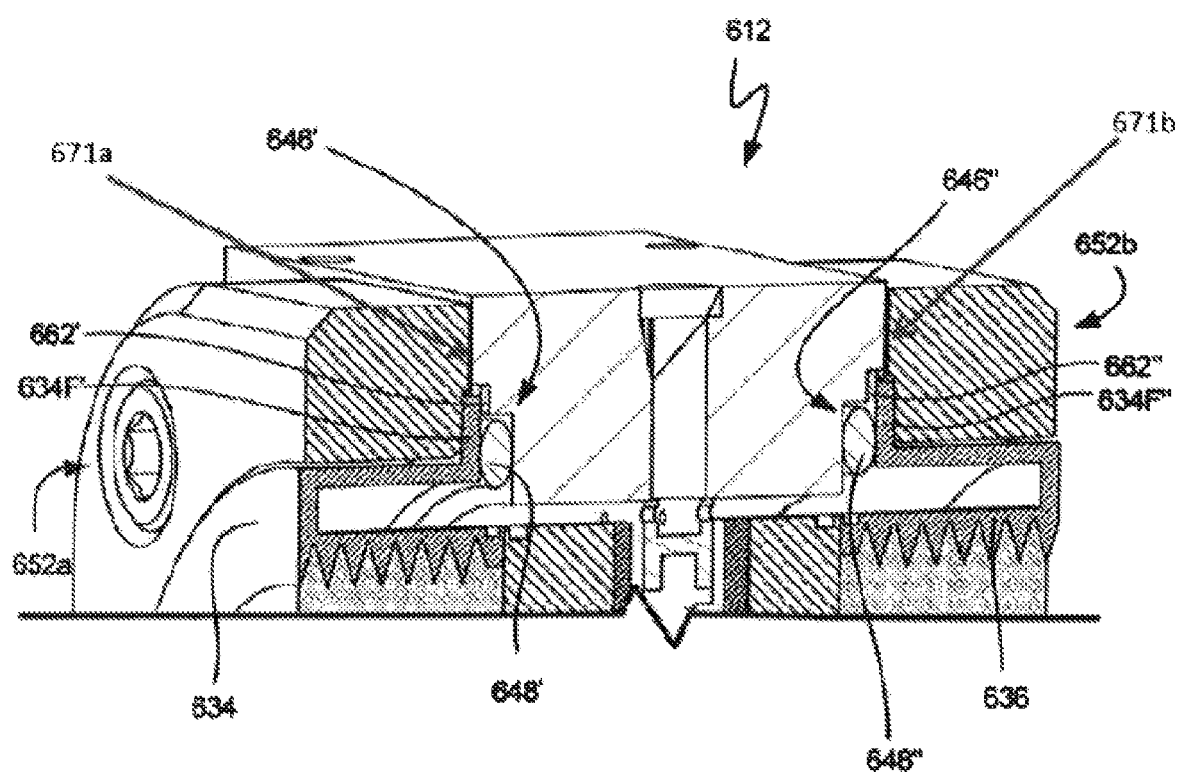
FIG. 7 is a cross-sectional view of the landings of an acoustic cell with detection/emission elements attached, showing acoustically absorbing or reflecting pads, according to an embodiment.

FIG. 7 is a cross-sectional perspective view of a noise-reducing feature of an acoustic cell 612. Acoustic cell 612 includes landings 646' and 646" upon which adjacent structures can be mounted to acoustic cell 612. Flange 634F is separated from acoustic cell 612 by o-ring 648'. O-rings 648' and 648" can be made of any material that facilitates a seal between acoustic cell 612 and flanges 634F' and 634F", respectively, as well as preventing transmission of acoustic signal from flanges 634F' and 634F" to acoustic cell 612.

As shown in FIG. 7, however, there could still be acoustic transmission between brackets (652a and 652b) and acoustic cell 612. Pads 671a and 671b provides a portion of landings 646' and 646" on which brackets 652a and 652b can be in mechanical contact, but which have sufficiently low acoustical transmission properties, or sufficient mismatch between its acoustical properties and those of brackets 652a-b, to prevent transfer of undesirable noise. For example, in embodiments, pads 671a and 671b can be made of KAPTON® or another polymeric material disposed on landings 646' and 646".

Rings 662' and 662" behave as a hard stop on which flanges 634F' and 634F" can be in mechanical contact with acoustic cell 612. Rings 662' and 662" can be made of Teflon®, KAPTON® or another polymeric material, which have low an acoustical impedance property comparing to cell 612 and flanges 634F' and 634F", to prevent transfer of undesirable noise.

As a result of the reduction in noise transmission through brackets (652a and 652b), pads (671a and 671b), and O-ring (648' and 648"), the overall noise level is reduced and signal-to-noise ratio is increased (i.e., with respect to FIG. 6, cutoff 506 is lowered).

Figure 8:
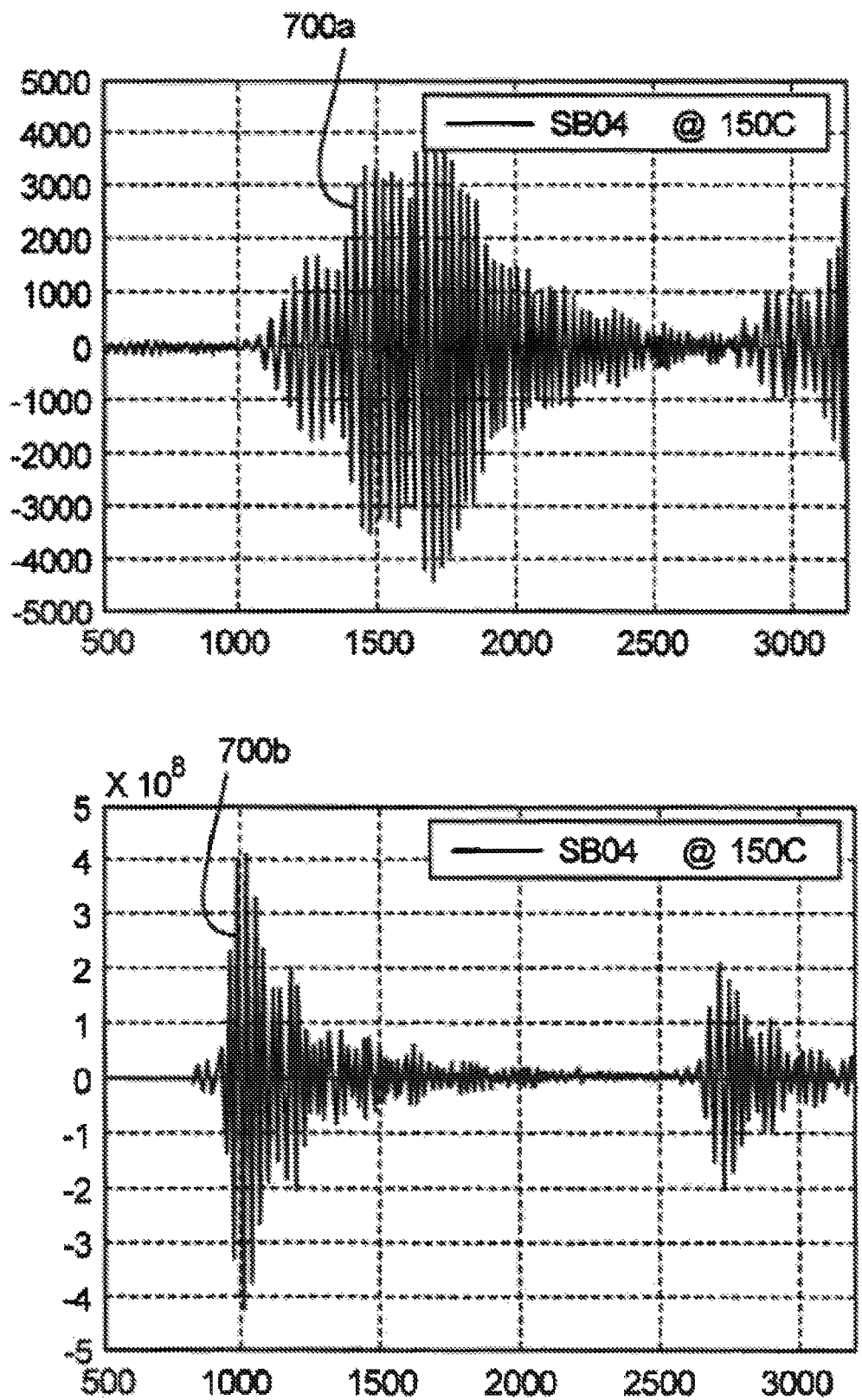
FIG. 8 is a chart of the electrical signal at used to determine time of flight of the acoustical signal, according to at least one embodiment.

FIG. 8 shows the signal produced at a pair of piezoelectric components. The left chart shows the received signal, and the right chart shows the "cross correlated signal" that is used to determine the "time of flight," as described in detail in U.S. Pat. No. 6,279,379, previously incorporated by reference in its entirety. The data shown in FIG. 8 was produced by a system (such as system 10 shown with respect to FIG. 1) having two piezoelectric components (e.g., 22 and 24 of FIG. 1), operating at 150° C. Between about timepoints 750 and 1500 a first pulse is emitted as shown in second sensor signal 700b. Between about timepoints 1250 and 2000 the pulse is received and re-emitted, as shown in first sensor signal 700a. Between about timepoints 2750 and 3250, the re-emitted signal is detected as shown in second sensor signal 700b.

The data shown in FIG. 8 are sufficiently clean (i.e., low noise) and have high enough amplitude (i.e., high signal) that, even operating at 150° C., the gas mixture between the sensors can be analyzed. This is a result of the use of the features described in embodiments above, such as: use of a metal solder couplant between the piezoelectric components and the transformer; use of metallic material or metal couplant between multiple leaves of piezoelectric material on each side of the chamber; and use of an acoustically-absorbing or mismatched pad to prevent undesirable acoustic data transmission through the acoustic cell.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112(f) of 35 U.S.C. are not to be invoked unless the specific terms "means for" or "step for" are recited in a claim.

What is claimed is:

1. An apparatus for determining gas concentration comprising:
    an acoustic cell defining a chamber;

a transmitter comprising:
  a first transducer configured to transmit an acoustic signal;
  a first dampener arranged between the acoustic cell and the first transducer; and
  a first transformer arranged between the chamber and the first transducer, the first transformer coupled to the first transducer with a metallic material, wherein the metallic material is configured to inhibit separation of the first transducer from the first transformer when subjected to temperatures greater than 150° C. the metallic material having a coefficient of thermal expansion between a coefficient of thermal expansion of the first transformer and a coefficient of thermal expansion of the first transducer; and
a receiver comprising:
  a second transducer configured to receive the acoustic signal;
  a second dampener arranged between the acoustic cell and the second transducer; and
  a second transformer arranged between the chamber and the second transducer, the second transformer coupled to the second transducer with the metallic material, wherein the metallic material is configured to inhibit separation of the second transducer from the second transformer when subjected to temperatures greater than 100° C., the metallic material having a coefficient of thermal expansion between a coefficient of thermal expansion of the second transformer and a coefficient of thermal expansion of the second transducer.

2. The apparatus of claim 1, wherein the metallic material is a solder.

3. The apparatus of claim 1, wherein the first transducer includes a piezoelectric element.

4. The apparatus of claim 3, wherein the first transducer includes a stack of piezoelectric elements, and wherein the stack of piezoelectric elements are coupled to one another by the metallic material.

5. The apparatus of claim 4, wherein the second transducer comprises a second stack of piezoelectric elements, and wherein the second stack of piezoelectric elements are coupled to one another by the metallic material.

6. The apparatus of claim 1, wherein a precursor gas inlet is configured to route a precursor gas through the apparatus during operation of a chemical vapor deposition or atomic layer deposition system.

7. The apparatus of claim 1, wherein the apparatus is configured to operate at pressures of less than 100 Torr.

8. The apparatus of claim 7, wherein the apparatus is configured to operate at pressures of less than 20 Torr.

9. The apparatus of claim 1, wherein the metallic material has a thickness of between about 25-50 μm.

10. The apparatus of claim 1, wherein the coefficient of thermal expansion of the metallic material is about $2.2 \times 10^{-5}$/deg-C.

* * * * *